United States Patent [19]

Bickel et al.

[11] 4,025,509
[45] May 24, 1977

[54] AMINOPYRIDINIUM ACETYL CEPHALOSPORANES

[75] Inventors: Hans Bickel, Binningen; Johannes Mueller, Arlesheim, both of Switzerland

[73] Assignee: Ciba-Geigy Corporation, Ardsley, N.Y.

[22] Filed: Apr. 24, 1975

[21] Appl. No.: 571,181

Related U.S. Application Data

[62] Division of Ser. No. 239,802, March 30, 1972, Pat. No. 3,929,779.

[52] U.S. Cl. .............................. 260/243 C; 424/246
[51] Int. Cl.² ....................................... C07D 501/20
[58] Field of Search .............................. 260/243 C

[56] References Cited
UNITED STATES PATENTS

| | | | |
|---|---|---|---|
| 3,516,997 | 6/1970 | Takano et al. | 260/243 C |
| 3,929,779 | 12/1975 | Bickel et al. | 260/243 C |

*Primary Examiner*—Nicholas S. Rizzo
*Attorney, Agent, or Firm*—Joseph G. Kolodny; John J. Maitner; Theodore O. Groeger

[57] ABSTRACT

Compounds of the formula

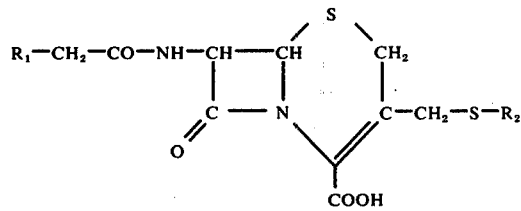

in which $R_1$ represents an aminopyridinium radical and $R_2$ a heterocyclic radical of aromatic character, bonded to the sulphur atom via a carbon atom, and containing at least 2 nitrogen atoms and additionally a further hetero-atom selected from nitrogen, oxygen and sulphur. They have antimicrobial activity.

5 Claims, No Drawings

AMINOPYRIDINIUM ACETYL CEPHALOSPORANES

This application is a divisional application of 239,802 filed on Mar. 30, 1972, now U.S. Pat. No. 3,929,779.

The present invention provides therapeutically active derivatives of 7-amino-cephalosporanic acid of the general formula I

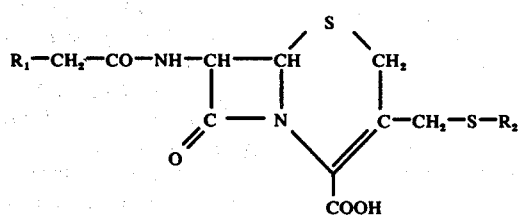

wherein $R_1$ denotes an aminopyridinium radical and $R_2$ represents a heterocyclic radical of aromatic character, bonded to the sulphur atom via a carbon atom, and containing at least 2 nitrogen atoms and additionally a further hetero-atom selected from nitrogen, oxygen and sulphur atoms, and esters, and salts of these compounds. The pyridinium radical contains the amino group in the ortho-, meta- or, preferably, para-position. It can possess yet further substituents, especially lower alkyl groups, such as, for example, methyl or ethyl radicals. The invention also provides a process for the manufacture of these compounds.

The heterocyclic radical $R_2$ has 5 or 6, preferably 5, ring atoms, but can be bonded to a fused benzene ring. Both rings can be substituted by aliphatic or aromatic hydrocarbon radicals, especially lower alkyl radicals containing from 1 to 5 carbon atoms, for example, methyl, ethyl, propyl, isopropyl, n-butyl, isobutyl and tert.butyl radicals; lower alkoxy or lower alkylthio radicals containing from 1 to 5 carbon atoms; in particular methylthio; cycloalkyl radicals, for example, cyclopentyl or cyclohexyl radicals, or aryl radicals, for example, phenyl or substituted phenyl radicals, for example, phenyl radicals substituted by one or more nitro groups or halogen atoms, or lower alkyl or lower alkoxy groups, or by substituted or unsubstituted thienyl, especially thienyl-2 radicals, the substituents being the same as indicated for phenyl; or optionally mono- or disubstituted amino groups, for example acetylamino, tert-.butyloxycarbonylamino, tert.amyloxycarbonylamino, or sulphonylamino groups. As examples of the heterocyclyl radical there should be mentioned: 1H-1,2,3-triazol-5-yl, 1,3,4-triazol-2-yl, 5-methyl-1,3,4-triazol-2-yl, 1H-1,2,4-triazol-5-yl, 1-phenyl-3-methyl-1H-1,2,4-triazol-5-yl, 4,5-dimethyl-4H-1,2,4-triazol-3-yl, 4-phenyl-4H-1,2,4-triazol-3-yl, 1H-tetrazol-5-yl, 1-methyl-1H-tetrazol-5-yl, 1-ethyl-1H-tetrazol-5-yl, 5yl, 1-n-propyl-1H-tetrazol-5-yl, 1-isopropyl-1H-tetrazol-5-yl, 1-n-butyl-1H-tetrazol-5-yl, 1-cyclopentyl-1H-tetrazol-5-yl, 1-phenyl-1H-tetrazol-5-yl, 1-p-chlorophenyl-1H-tetrazol-5-yl, 1,2,3-thiadiazol-5-yl, 1,3,4-thiadiazol-2-yl, 1,2,4-thiadiazol-3-yl, 1,2,4-thiadiazol-5-yl, 3-methyl-1,2,4-thiadiazol-5-yl, 2-methyl-1,3,4-thiadiazol-5-yl, 2-methylthio-1,3,4-thiadiazol-5-yl, 2-ethyl-1,3,4-thiadiazol-5-yl, 2-n-propyl-1,3,4-thiadiazol-5-yl, 2-isopropyl-1,3,4-thiadiazol-5-yl, 2-phenyl-1,3,4-thiadiazol-5-yl, 1,2,4-oxadiazol-5-yl, 1,2,3-oxadiazol-5-yl, 1,3,4-oxadiazol-5-yl, 2-methyl-1,3,4-oxadiazol-5-yl, 2-ethyl-1,3,4-oxadiazol-5-yl, 2-phenyl-1,3,4-oxadiazol-5-yl, 2-p-nitrophenyl-1,3,4-oxadiazol-5-yl, 2[thienyl(2)]-1,3,4-oxadiazol-5-yl and thiatriazol-5-yl, as well as corresponding radicals containing 6 ring atoms.

The compounds of the invention possess a particularly good antibacterial action. They are active both against gram-positive bacteria and against gram-negative bacteria, for example against penicillin-resistant *Staphylococcus aureus*, *Escherichia coli*, *Klebsiella pneumoniae* and *Salmonella typhosa*, as is shown in animal experiments, for example, on mice. They can therefore be used for combating infections which are caused by such micro-organisms, and also as additives to animal feeds, for preserving foodstuffs, or as disinfectants. Particularly valuable compounds are those of the formula I, in which $R_1$ is the para-aminopyridinium radical and $R_2$ is a tetrazol-5-yl or 1,2,4- or 1,3,4-thiadiazol-5-yl radical which is optionally substituted, for example, by methyl radicals.

The compounds of the present invention can be manufactured by methods which are known for the manufacture of analogous compounds. The term "known" is used herein to mean in actual use or described in the literature of the art. Thus they are obtained i. if a compound of the formula II

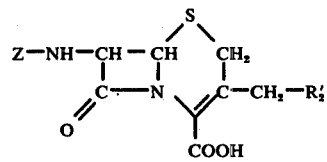

wherein Z represents the acyl radical $R_1'$ —$CH_2$ — CO —, in which $R_1'$ represents an aminopyridinium radical optionally protected by a removable protective group, and $R_2'$ represents a functionally modified, especially an esterified, hydroxyl group, for example, a hydroxyl group esterified by a mineral acid, for example, a hydrohalic acid, for example, hydriodic acid or hydrofluoric acid, especially hydrobromic acid or hydrochloric acid, or by a carboxylic acid, for example, a lower alkanoic acid which is unsubstituted or substituted, for example by a halogen atom, for example, propionic acid or chloroacetic acid, especially acetic acid, or an aryl carboxylic acid or aryl-lower alkylcarboxylic acid, for example, benzoic acid or phenylacetic acid, or an ester or a salt thereof, is reacted with a thiol of the formula Ib HS—$R_2$   Ib in which $R_2$ has the meaning given for the formula I or with a metal salt thereof, or (ii) if a compound of the formula II, wherein Z represents a reactive esterified hydroxyacetyl group and $R_2'$ represents S—$R_2$, or a salt or an ester of this compound, is reacted with an aminopyridine which is optionally protected by a removable protective group, or (iii) if a compound of the formula II wherein Z represents hydrogen and $R_2'$ represents S—$R_2$, or a salt or an ester thereof is reacted with an acylating agent which contains the acyl radical Z, for example with a compound of the formula $R_1'$ — $CH_2$ — COOH, in which $R_1'$ has the meaning given herein above, or with a reactive acid derivative thereof, and from the resulting compounds containing a protective amino group the protective group is split off, and, if desired, an ester group which may be present is split off, and, if desired, the resulting compounds are converted into acid addition salts or metal salts, for example alkali or alkaline earth metal salts, or salts with ammonia or organic bases, or from resulting salts the inner salts are formed.

A reactive esterified hydroxyl group is especially a hydroxyl group esterified by a strong inorganic acid, for example, a lower alkylsulphonic acid or an arylsulphonic acid, for example, toluenesulphonic acid. Above all, it is a hydroxyacetyl group esterified by a hydrohalic acid, for example, hydrofluoric, hydrochloric, hydriodic or especially hydrobromic acid.

The compounds used as starting materials are known or may be manufactured by methods which are known in the art. Compounds of the formula II, wherein $R_2'$ represents an esterified hydroxy group, primarily the acetoxy group, and Z represents an optionally protected aminopyridiniumacetyl radical, and their manufacture, are described in German Offenlegungsschrift DT 2 048 436 (Swiss Application No. 15269/69, Case 4-6866). Salts thereof are, for example salts with alkali or alkaline earth metals or with zinc or with organic bases, for example triethylamine, diisopropylamine, ethanolamine. Compounds of the formula II, wherein Z represents a reactive esterified hydroxyacetyl group, e.g. halogenoacetyl, in particular bromoacetyl, and $R_2'$ represents $S-R_2$, are obtained, for example, by reacting 7-aminocephalosporanic acid (7-ACA) in the same way as indicated in the case of 7-aminopyridiniumacetylaminocephalosporanic acid with a thiol or salt thereof, and then substituting the resulting compound at the 7-amino group, for example by a halogenoacetyl radical, in particular a bromoacetyl radical. Instead of 7-ACA, it is also possible to use cephalosporin C as starting material and to split off the aminoadipoyl radical after the reaction with the thiol, for example by conversion into a halogenoimide, then into an iminoether, which latter is hydrolysed as described, for example, in French Patents No.'s 1 394 820 or 95 581. Compounds of the formula II, wherein Z represents hydrogen and $R_2'$ represents $S - R_2$, can be obtained by both the routes indicated hereinabove.

A metal salt of the thiol is in particular an alkali metal salt, for example, a sodium salt or potassium salt. The salt can be manufactured, for example, by reaction of the thiol with a carbonate, bicarbonate or hydroxide of the alkali metal.

Protective groups for the amino groups are those which can be easily split off, for example by solvolysis, such as removal with water or alcohols, optionally in a weak basic (up to pH 10) or preferably acid medium, or by photolysis.

The amino group can be protected, for example, by easily removable acyl groups, in particular by acyl groups which are derived from carbonic acid. As examples of radicals of this kind which can be removed under acid conditions, for example by treatment with a strong organic carboxylic acid, such as a halogeno-lower alkanecarboxylic acid, primarily trifluoroacetic acid, there may be cited: optionally substituted carbo-lower alkoxy radicals, chiefly carbo-lower alkoxy groups which are polybranched in α-position, or carbo-lower alkoxy groups which contain in α-position cyclic substituents of aromatic character, such as aromatic groups, for example phenyl or biphenylyl radicals, for example 4-biphenylyl radicals, or heterocyclic groups of aromatic character, for example 2-furyl radicals, in particular the carbo-tert.butyloxy and carbo-tert. pentyloxy radical, the carbo-diphenylmethoxy, carbo-2-(4-biphenylyl)-2-propyloxy, carbo-1,1-diphenylethoxy or carbo-2-furfuryloxy radical, and carbo-cycloalkoxy radicals in which cycloalkyl preferably represents a polycyclic cycloalkyl group, in particular the carboadamantyloxy radical.

Carbo-lower alkoxy groups in which the lower alkyl radical, in particular the methyl radical, contains a α-position one or two phenyl groups substituted by lower alkoxy, chiefly methoxy and/or nitro, for example m-methoxybenzyl, 3,5-dimethoxybenzyl, 3,4-dimethoxy-6-nitrobenzyl, di-(para-methoxyphenyl)-methyl, α-phenyl-α-(3,4-dimethoxy-6-nitrophenyl)-methyl,α-methyl-α-(3,4-dimethoxy-6-nitrophenyl)-methyl, can also be split off in known manner photolytically, for example by irradiation with ultraviolet light, preferably with a high-pressure mercury-vapour lamp.

Further amino protective groups are, for example, polyarylmethyl groups, wherein aryl represents preferably an optionally substituted phenyl group, in particular the trityl group. Such groups can be split off in known manner, for example by treatment with suitable acid agents, such as a strong inorganic acid, for example hydrochloric acid, or with an organic acid, for example formic or acetic acid.

Esters of compounds of the formula II are those in which the carboxyl group is esterified in the 4-position of the dihydrothiazine ring. Since the ester group, if necessary or desired, is to be split off, suitable esters are those which — besides esters which are readily therapeutically useful — can be easily split off, for example solvolytically, hydrogenolytically, by nucleophilic exchange, or photolytically, to give the free carboxylic acid.

It is thus possible to convert a carbo-lower alkoxy group, in which lower alkyl is polybranched in α-position and/or contains in α-position radicals of aromatic character, such as optionally substituted aromatic hydrocarbon groups, for example phenyl radicals, or heterocyclic groups or aromatic character, such as the 2-furyl group, for example the carbotert.butyloxy or carbo-tert.pentyloxy group, or the carbo-di-phenylmethoxy or carbo-2-furfuryloxy group, also a carbocycloalkoxy group, in which cycloalkyl represents a polycyclic radical, such as the carbo-adamantyloxy group, into the free carboxyl group by treatment with a suitable acid agent, for example a strong organic carboxylic acid, preferably a halogen-containing lower alkanecarboxylic acid, above all trifluoroacetic acid.

Further esterified carboxyl groups which can easily and under mild conditions be converted into the free carboxyl group are silylated and stannylated carboxyl groups. These are groups which can be formed on treatment of a compound having a free carboxyl group, as well as a salt, thereof, for example an alkali metal salt, for example, a sodium salt thereof, with a suitable silylating agent, for example, a tri-lower alkyl silyl halide, for example, trimethyl-silyl halide, or an N-(tri-lower alkylsilyl)-N-$R_a$—$R_b$-amine, wherein $R_a$ represents a hydrogen atom or a lower alkyl group and $R_b$ represents a hydrogen atom, a lower alkyl group or a tri-lower alkyl-silyl group (see, for example, British Pat. No. 1,073,530), or with a suitable stannylating agent, for example, a bis-(tri-lower alkyl-tin) oxide, for example, bis-(tri-n-butyl-tin) oxide, a tri-lower alkyl-tin hydroxide, for example, tri-ethyl-tin hydroxide, a tri-lower alkyl-lower alkoxy-tin compound, tetra-lower alkoxytin compound or tetra-lower alkyl-tin compound, as well as a trilower alkyl-tin halide, for example, tri-n-butyl-tin chloride (see, for example, Netherlands Published Specification 67/17,107). The above-mentioned starting substances with silylated or stannylated carboxyl groups can be converted into the desired compounds having a free carboxyl group, for example, by treatment with a preferably neutral hydrogen donor, especially water or an alcohol, for example, a lower alkanol, for example, ethanol.

Esters which are as such therapeutically useful are, for example, esters such as are described in British Pat. No. 1,229,453 and in German Offenlegungsschrift DT 1,951,012. These esters are distinguished by the fact that they are easily absorbed in the organism. The esters are derived from alcohols of the formula HO-CH$_2$OCO—R, wherein R may represent a hydrogen atom, an alkyl radical, a cycloalkyl radical, a cycloalkylalkyl radical, an aryl radical, an aralkyl radical or a heterocyclyl radical. In particular, R may represent a lower alkyl radical containing at most 5 carbon atoms, such as methyl, ethyl, propyl, isopropyl, butyl, isobutyl, chiefly tert.butyl, also a mono-cyclic cycloalkyl radical containing from 3 to 7 carbon atoms, a bicyclic cycloalkyl radical, such as a 1-bicyclo-(2,2,2)octyl or adamantyl radical, a monocyclic aryl radical, for example an optionally substituted phenyl radical, a bicyclic aryl radical, such as a 1-naphthyl, 2-naphthyl or a substituted naphthyl radical, a mono- or bicyclic aralkyl radical, for example a benzyl or phenylethyl radical or a naphthyl-lower alkyl radical, such as naphthylmethyl. R may also represent a heterocyclyl radical containing from 5–6 ring atoms and having at least one nitrogen, sulphur or oxygen atom, for example thienyl, furyl, pyrryl, oxazoyl, thiazolyl, imadazoyl.

Examples of substituents in the above ring systems which form a part of R include lower alkyl radicals, lower alkoxy radicals, lower alkylmercapto radicals, lower halogenalkyl radicals, such as mono-, di- or trihalogenoalkyl radicals, in which halogen may be fluorine, chlorine or bromine, and also nitro groups. Processes for the manufacture of the above esters are described in the cited British patent and German application.

The reaction with the thiol is carried out as described in Belgian Pat. No. 617,687 or in Netherlands Application No. 6,805,179, in an inert solvent, for example, an alcohol, ether, ketone or N,N-disubstituted amide, for example, dimethylformamide or dimethylacetamide, when using a salt, preferably in a water-miscible inert solvent or in a mixture of water and such a solvent, for example in acetone, methanol, ethanol, dioxane, tetrahydrofurane or their aqueous solutions, preferably in aqueous acetone. The reaction temperature is from +15° to 70° C, preferably from 40° to 60° C. The pH of the solution is preferably kept from 5.0 to 7.5. If necessary, a buffer, for example, sodium acetate or, if the compound is used in the form of an alkali metal salt, for example acetic acid is added.

The reaction of the compound II, wherein $R_2'$ represents $S - R_2$ and $R_1'$ represents a reactively esterfied hydroxyl group, with an aminopyridine takes place at room temperature or at slightly elevated or lowered temperature, preferably from 20° to 40° C. It is preferably carried out in the presence of an agent which binds hydrogen halides, for example, a tertiary amine, especially a tri-lower alkylamine, preferably diisopropylethylamine (Hunig base).

The acylation of the compound II, wherein $R_2'$ represents S—$R_2$ and Z represents hydrogen, is carried out in known manner, in particular by the methods known in the art for acylating weak basic amino groups by aminoacids. In this reaction, the amino group in the acyl radical need not necessarily be protected. For example, one procedure to be followed is that the compound II is reacted with an acid addition salt, in particular the salt of a hydrohalic acid as mentioned hereinabove, for example the hydrochloride of an acid halide e.g. fluoride, bromide, iodide, primarily the acid chloride, of an acid of the formula $R_1 - CH_2 - COOH$. Further, the acylation can be carried out by treating the compound II with an N-carboxyanhydride (Leuch's anhydride) of an acid of the formula $R_1$—CH$_2$—COOH. Preferably the amino group in the acyl radical is protected as mentioned above and the acylation carried out in the manner known for the synthesis of peptides, for example by the carbodiimide method or analogous methods accompanied by the use of a condensing agent, or by the azide method, the method of activated esters, or the method of mixed anhydrides.

Preferably, those starting substances are used which lead to the particularly active end products which have been mentioned.

The invention relates also to those embodiments of the process in which a compound obtainable as an intermediate product at any stage of the process is used as starting material and the missing steps of the process are carried out, or the process is discontinued at any stage, or in which a starting material is formed under the reaction conditions, or in which the reactants are optionally present in the form of their salts.

Depending on the procedure, the compounds of the invention are obtained in the form of bases or of their salts. A base can be obtained from a salt in a manner which is in itself known. In turn, a base can be reacted with an acid which is suitable for the formation of a physiologically tolerable salt, to give a salt, for example, with an inorganic acid, for example, a hydrohalic acid, for example, hydrochloric acid or hydrobromic acid, perchloric acid, nitric acid, or thiocyanic acid, sulphuric acid or phosphoric acid, or an organic acid, for example, formic acid, acetic acid, propionic acid, glycollic acid, lactic acid, pyruvic acid, oxalic acid, malonic acid, succinic acid, maleic acid, fumaric acid, malic acid, tartaric acid, citric acid, ascorbic acid, hydroxymaleic acid, dihydroxymaleic acid, benzoic acid, phenylacetic acid, 4-aminobenzoic acid, 4-hydroxybenzoic acid, anthranilic acid, cinnamic acid, mandelic acid, salicylic acid, 4-amino-salicyclic acid, 2-phenoxybenzoic acid, 2-acetoxybenzoic acid, methanesulphonic acid, ethanesulphonic acid, hydroxyethanesulphonic acid, benzenesulphonic acid, p-toluenesulphonic acid, naphthalenesulphonic acid or sulphanilic acid.

The compounds of the invention can be used as medicines, for example in the form of pharmaceutical preparations. These comprise the compounds in admixture or conjunction with a pharmaceutical organic or inorganic, solid or liquid carrier suitable for enteral, topical or parenteral administration. Possible carriers are those which do not react with the compounds of the invention, such as, for example, water, gelatine, lactose, starch, stearyl alcohol, magnesium stearate, talc, vegetable oils, benzyl alcohols, gum, propylene glycol, polyalkylene glycols, white petroleum jelly, cholesterol or other known medicinal excipients. The pharmaceutical preparations can, for example, be in the form of tablets, dragees, ointments, creams or capsules or in a liquid form, as solutions, suspensions or emulsions. They are optionally sterilised and/or contain auxiliary substances, such as preservatives, stabilisers, wetting agents or emulsifiers, solubilising agents or salts for regulating the osmotic pressure or buffers. They can also contain other pharmaceutically useful substances. The preparations are obtained in accordance with customary methods.

The following Examples illustrate the invention.

The following systems are used in the thin layer chromatography (colouration by iodine spray):
System 52A = n-Butanol-glacial acetic acid-water (67:10:23)
System 101 = n-Butanol-pyridine-glacial acetic acid-water (38:24:8:30)
System 101D = n-Butanol-pyridine-glacial acetic acid-water (34:24:12:30)
System 110 = n-Butanol-ethyl acetate-pyridine-glacial acetic acid-water (42:21:21:6:10)
System 69 = ethyl acetate-glacial acetic acid water (60:20:20).

In the Examples, "MIC" means the minimum inhibitory concentration which is measured by the gradient plate test described in "Antibiotics" Vol. I by Gottlieb and Shaw, New York, 1967, page 508, a modified method of that described by V. Bryson and R. Szybalski, Science 116, 45 (1952). The MIC is determined on strains of Staphylococcus aureus SG 511 (sensitive to penicillin) or Staphylococcus aureus 2999 (resistent to penicillin), Bacillus megatherium, Escherichia coli 2018, Klebsiella pneumoniae and/or Salmonella typhimuri.

EXAMPLE 1

2.2 g of 7-bromoacetylamino-3-(1-methyl-tetrazol-5-ylthio)-methyl-ceph-3-em-4-carboxylic acid are dissolved in 20 ml of dry methanol and treated with 0.86 ml of N,N-diisopropylethylamine. 465 mg of 4-aminopyridine are added and the mixture is left to stand for 18 hours at room temperature. A crude precipitate is obtained by adding 20 ml of ethyl acetate. After removing the liquid, which can be decanted, this precipitate is triturated with 20 ml of a mixture of water and methanol (1:1). Thereupon, a resin deposits on the walls of the vessel. The supernatant solution is separated off, treated with 200 ml of absolute ethanol and left to stand for several hours at −10° C. 7-[(para-Aminopyridinium)-acetylamino]-3-(1-methyl-tetrazol-5-ylthio)-methyl-ceph-3-em-4-carboxylic acid is thus obtained as a colourless powder. In the ultra-violet spectrum (in water) $\lambda_{max}$ = 271 nm.

In the thin layer chromatogram on silica gel, $Rf_{52A}$ = 0.08, $Rf_{101}$ = 0.37, $Rf_{101D}$ = 0.48 and $Rf_{110}$ = 0.07. MIC : St. aureus 511 = 0.2 γ/ml; Staph. aureus 2999 = 0.55 γ/ml; Bac. meg. = γ/ml; E. coli = 10 γ/ml; K. pneum. = 4 γ/ml; S. typh. =10 γ/ml.

The starting material can be manufactured as follows:

a. 50 g of 7-aminocephalosporanic acid and 25.75 g of 5-mercapto-1-methyltetrazol are suspended in a mixture of 300 ml of water and 500 ml of acetone. The substances are dissolved by gradual addition of 370 ml of saturated sodium bicarbonte solution (pH = 6.8). The reaction mixture is is then warmed to 60° C over the course of 5½ hours in a nitrogen atmosphere, whilst stirring. After cooling, the acetone is evaporated off in vacuo and the aqueous solution is adjusted to pH 4 by adding approx. 60 ml of 4 N hydrochloric acid. The mixture is left to stand overnight in a refrigerated chamber and the precipitate is filtered off, washed with a little cold water and then rinsed with a large amount of acetone. The crude precipitate thus obtained is further purified by again dissolving it in water using sodium bicarbonate (pH 7), filtering the solution through "Norit" and "Celite" and the product is precipitated by means of hydrochloric acid (pH 4). The product is directly used for the further reaction.

b. 20 g of 7-amino-3-(1-methyl-tetrazol-5-ylthio)methylceph-3-em-4-carboxylic acid are dissolved in 460 ml of dimethylformamide and 15.7 ml of triethylamine. This solution is added dropwise over the course of 25 minutes, whilst stirring vigorously, to a solution, precooled to −20° C, of 14.1 g of bromoacetyl bromide in 115 ml of methylene chloride. During the addition the temperature is kept low, and then the batch is allowed to warm to room temperature and is finally stirred for a further hour at room temperature. Thereafter, the reaction mixture is filtered through a "Celite" layer and is concentrated to a syrupy consistency in a high vacuum, using a solid carbon dioxide/acetone condenser. The residue obtained is taken up in 160 ml of 10% strength phosphate buffer of pH 6.7, and 500 ml of ethyl acetate. A pH of 6.0 is established by stirring and adding a total of 37 ml of 20% strength dipotassium hydrogen phosphate solution. After separating the phases, the aqueous phase is again re-extracted with 500 ml of ethyl acetate. The organic phases are discarded. The aqueous phase is now covered with 1.5 liters of ethyl acetate and is brought to pH 2.8 with strong acid. After the phase separation, the aqueous phase is re-extracted with 1.2 and 1.0 liter of ethyl acetate. The organic phases are successively washed with twice 100 ml of saturated sodium chloride solution, dried by means of sodium sulphate and evaporated to dryness in vacuo. The light-coloured resin is dissolved in 60 ml of acetone. An impurity is precipitated by adding 70 ml of absolute ether, and the decanted liquid is treated with 600 ml of ether and 700 ml of pentane whilst stirring vigorously. 7-Bromoacetylamino-3-(1-methyl-tetrazol-5-ylthio)-methyl-ceph-3-em-4-carboxylic acid is obtained as an almost colourless precipitate which can directly be used further.

EXAMPLE 2

203 mg (0.5 mmol) of 7-[(para-aminopyridinium)-acetylamino]-cephalosporanic acid are dissolved in 10 ml of 5% strength phosphate buffer of pH 6.7, while warming to approx. 30° C. 116 mg of solid 5-mercapto-1-methyl-tetrazole are then added and the pH is adjusted to 6.5 by means of 2.0 ml of a 10% strength solution of dipotassium hydrogen phosphate, whereupon all the material dissolved. The mixture is now stirred for 6 hours at 60° C under nitrogen. After cooling to 0° C, a ten-fold volume of methanol at 0° C (120 ml) is added to the solution whilst stirring vigorously. The whole is left to stand for 1 hour at 0° C and the phosphate which has crystallised is filtered off. For dehydration, the filtrate is repeatedly treated with 100 ml portions of absolute ethanol and concentrated in vacuo. Finally, a little ethyl acetate is added, the mixture is left to stand for 1 hour at 0° C and is filtered, and a crude precipitate which still contains phosphate is obtained. 7-[(para-Aminopyridinium)acetylamino]-3-(1-methyl-tetrazol-5-ylthio)methylceph-3-em-4-carboxylic acid can be obtained as a colourless powder by trituration with dry methanol, filtering and precipitation from the filtrate by means of ethanol and ethyl acetate. The compound is dissolved in 1 ml of water and the solution is filtered through a column of 25 ml of Sephadex G 10 (diameter 1.4 cm). The first 15 ml of eluate are discarded and the subsequent 6 ml of eluate contain the substance. The eluate is treated with 50 ml of absolute ethanol and concentrated in vacuo to a volume of approx. 2 ml, and the product is precipitated by means of 10 ml of ethyl acetate. In the thin layer chromatogram, the precipitate has the same Rf-values as the product described in Example 1. In the ultraviolet spectrum (in water)$\lambda_{max} = 271$ nm ($\epsilon = 30,600$). The optical rotation is $[\alpha]_D^{20} = 452° \pm 1°$ (c = 0.9 in water).

The starting material can be manufactured as follows:

3.9 g of 7-bromoacetylaminocephalosporanic acid are dissolved in 20 ml of methanol with the addition of 1.7 ml of N,N-diisopropylethylamine. 0.94 g of 4-aminopyridine is added and the solution is left to stand for 12 hours at room temperature. 7-[(para-Aminopyridinium)-acetylamino]-cephalosporanic acid is precipitated as an amorphous powder by slow addition of ethyl acetate. The substance dissolves in warm methanol-water (1:1) and crystallises on cooling in colourless platelets which decompose from 120° C onwards, without melting.

In thin layer chromatography on silica gel, the following Rf-values are obtained after colouration with iodine vapour:

$Rf_{52A} = 0.10$
$Rf_{101} = 0.25$
$Rf_{101D} = 0.37$.

EXAMPLE 3

3.95 g of 7-[(para-aminopyridinium)acetylamino]-cephalosporanic acid are dissolved in 195 ml of 5% strength phosphate buffer of pH 6.7 by warming to approx. 30° C. 2.56 g of solid 5-mercapto-2-methyl-1,3,4-thiadiazole are then added and the pH is adjusted to 6.5 by means of 20 ml of a 10% strength solution of dipotassium hydrogen phosphate, whereupon all the material dissolves. The mixture is now stirred for 6 hours at 60° C under nitrogen. After cooling to 0° C, 2 litres of methanol at 0° C are added to the solution, with vigorous stirring. The mixture is stirred for a further half hour at 0° C and the phosphate which has crystallised is filtered off. The filtrate is first concentrated in vacuo to a volume of approx. 50 ml and is then dehydrated by twice treating with 1.2 litres of absolute ethanol at a time and concentrating in vacuo to a volume of 200 ml. Finally, 300 ml of ethyl acetate are added, the mixture is left to stand for one hour at 0° C and is filtered and the product is washed with ethyl acetate to yield a crude precipitate (6.04 g) which still contains phosphate. This is dissolved in 40 ml of water and filtered through a column of 1,500 ml of Sephadex G 10 (diameter 4.7 cm). The first 880 ml of eluate ar discarded and the subsequent 330 ml of eluate contain the reaction product. They are carefully concentrated to a volume of approx. 100 ml in vacuo, mixed with 100 ml of methanol, treated with active charcoal and then concentrated in vacuo to a volume of approx. 30 ml. Hereupon, 7-[(para-aminopyridinium)acetylamino]-3-(2-methyl-1,3,4-thiadiazol-5-ylthio) methylceph-3-em-4-carboxylic acid is obtained as colourless crystal needles of decomposition point 170° C (sealed in vacuo).

In the thinlayer chromatogram on silica gel, $Rf_{52A} = 0.07$, $Rf_{101} = 0.35$ and $Rf_{110} = 0.05$ (colouration by spraying with iodine).

In the ultra-violet spectrum (in 2:1, water-methanol), $\lambda_{max}$ is 272 nm ($\epsilon = 36,200$). The optical rotation $[\alpha]_D^{20} = +3°\pm1°$ (c = 1.2 in 2:1, water-methanol). MIC: St. aureus 511 = 0.1 γ/ml; St. aureus 2999 = 0.6 γ/ml; E.coli = 10 γ/ml; K.pneum. = 5 γ/ml.

The starting material can be manufactured as described in Example 2.

EXAMPLE 4

8.13 g of 7-[(para-aminopyridinium)acetylamino]-cephalosporanic acid are dissolved in 350 ml of 5.7% strength phosphate buffer of pH 6.7 by warming to approx. 30° C. 4.73 g of solid 2-mercapto-1,3,4-thiadiazole are then added and the pH is adjusted to 6.5 by means of 100 ml of a 10% strength solution of dipotassium hydrogen phosphate, whereupon all the material dissolves. The mixture is now stirred for 6 hours at 60° C under nitrogen. After cooling to 0° C, the solution is run into 4 litres of methanol at 0° C, whilst stirring vigorously. The mixture is stirred for a further half hour at 0° C and the phosphate which has crystallised is filtered off. The filtrate is then concentrated in vacuo to a volume of approx. 800 ml and in order to dehydrate it is concentrated in vacuo, with continuous addition of a total of 3 litres of absolute ethanol (through a capillary), to a volume of 400 ml. Finally, 600 ml of ethyl acetate are added, the mixture is left to stand for one hour at 0° C, the product is filtered and washed with ethyl acetate, and a crude precipitate (11.39 g) which still contains phosphate is obtained. 3.0 g of this product are dissolved in 20 ml of water and filtered through a column of 350 ml of Sephadex G 10 (diameter 3.5 cm). The first 210 ml of eluate are discarded and the subsequent 90 ml of eluate contain the reaction product. They are carefully concentrated in vacuo to a volume of approx. 25 ml, mixed with 25 ml of methanol, treated with active charcoal and then concentrated in vacuo to a volume of approx. 10 (sic). 20 ml of ethanol, followed by 60 ml of ether, are added to this solution whilst stirring well.

An almost colourless precipitate of 7-[(para-aminopyrimidinium)acetylamino]-3-(1,3,4-thiadiazol-2-ylthio)methylceph-3-em-4-carboxylic acid is thereby obtained, which decomposes at approx. 180° C, whilst turning brown.

In the thin layer chromatogram on silica gel, $Rf_{52}A = 0.11$, $Rf_{101} = 0.31$ and $Rf_{110} = 0.06$. MIC: St. aureus 511 = 0.2 γ/ml; St. aureus 2999 = 0.6 γ/ml; B.meg. = 7 γ/ml; E. coli = 20 γ/ml; K.pneum. = 5γ/ml; S.typh. = 10 γ/ml.

In the ultra-violet spectrum (in 2:1, water-methanol), $\lambda_{max}$ is 269 nm ($\epsilon = 34,200$). The optical rotation $[\alpha]_D^{20} = \pm 26° \pm 1°$ (c = 0.89 in 2:1, water-methanol).

EXAMPLE 5

8.13 g of 7-[(para-aminopyridinium)acetylamino]-cephalosporanic acid are dissolved in 350 ml of 5.7% strength phosphate buffer at pH 6.7 by warming to approx. 30° C. 4.65 g of solid 5-mercapto-2-methyl-1,3,4-oxadiazole are then added and the pH is adjusted to 6.5 by means of 110 ml of a 10% strength solution of dipotassium hydrogen phosphate, whereupon all the material dissolves. The mixture is now stirred for 6 hours at 60° C under nitrogen. After cooling to 0° C, the solution is run into 4 litres of methanol at 0° C whilst stirring vigorously. The mixture is stirred for a further half hour at 0° C and the phosphate which has crystallised is filtered off. The filtrate is then concentrated in vacuo to a volume of approx. 800 ml and is dehydrated by concentrating in vacuo, with continuous addition of a total of 3 litres of absolute ethanol (through a capillary), to a volume of 400 ml. Finally, 600 ml of ethyl acetate are added, the mixture is left to stand for one hour at 0° C and is filtered, the product is washed with ethyl acetate and a crude precipitate (5.19 g) which still contains phosphate is obtained. This is dissolved in 25 ml of water and filtered through a column of 750 ml of Sephadex G 10 (diameter 4.5 cm). The first 350 ml of eluate are discarded and the subsequent 110 ml of eluate contain the reaction product. They are carefully concentrated in vacuo to a volume of approx. 30 ml, treated with active charcoal and then concentrated in vacuo to a volume of approx. 10 ml. Hereupon, 7-[(para-aminopyridinium)acetylamino)]-3-(2-methyl-1,3,4-oxadiazol-5-ylthio)methylceph-3-em-4-carboxylic acid is obtained as colourless crystals of decomposition point 183° C (sealed in vacuo).

In a thin layer chromatogram on silica gel, $Rf_{52A} = 0.10$, $Rf_{101} = 0.36$ and $Rf_{110} = 0.05$. MIC: St. aureus 511 = 0.3 γ/ml; St. aureus 2999 = 0.7 γ/ml; B. meg. = 5 γ/ml.

In the ultraviolet spectrum (in water), $\lambda_{max}$ is 270 nm ($\epsilon = 34{,}200$). The optical rotation $[\alpha]_D^{20} = +3° \pm 2°$ (c = 0.54 in 0.1 molar $NaHCO_3$).

EXAMPLE 6

8.13 g of 7-[(para-aminopyridinium)acetylamino]-cephalosporanic acid are dissolved in 350 ml of 5.7% strength phosphate buffer of pH 6.7 by warming to approx. 30° C. 4.61 g of solid 5-mercapto-3-methyl-1,2,4-triazole are then added and the pH is adjusted to 6.5 by means of 3 ml of 20% strength phosphoric acid, whereupon all the material dissolves. The mixture is now stirred for 6 hours at 60° C under nitrogen. After cooling to 0° C, the solution is run into 4 litres of methanol at 0° C, with vigorous stirring. The mixture is stirred for a further half hour at 0° C and the phosphate which has crystallised is filtered off. The filtrate is first concentrated in vacuo to a volume of approx. 800 ml and is dehydrated by concentrating in vacuo, with continuous addition of a total of 3 litres of absolute ethanol (through a capillary), to a volume of 400 ml. Finally, 800 ml of ethyl acetate are added, the mixture is left to stand for one hour at 0° C and is filtered, the product is washed with ethyl acetate and a crude precipitate (10.37 g) which still contains phosphate is obtained. This is dissolved in 25 ml of water and is filtered through a column of 750 ml of Sephadex G 10 (diameter 4.5 cm). The first 360 ml of eluate are discarded and the subsequent 250 ml of eluate contain the reaction product. They are carefully concentrated in vacuo to a volume of approx. 300 ml, whereupon the reaction product separates out in a crystalline form. The crystals are suspended in a hundred-fold amount of water, the pH is adjusted to 2.0 by adding N hydrochloric acid, whereupon the crystals dissolve, and the solution is treated with a little active charcoal. The colourless solution of the hydrochloride, thus obtained, is concentrated in vacuo to a low volume and the hydrochloride is precipitaed by successive addition of ethanol and ether. The hydrochloride is a colourless, water-soluble powder.

In order to manufacture the base, the aqueous solution of the hydrochloride is adjusted to pH 7.5 by means of N $NH_4OH$ solution and is concentrated to a low volume in vacuo. Hereupon, 7-[(para-aminopyridinium)acetylamino]-3-(3-methyl-1,2,4-triazol-5-ylthio)methylceph-3-em-4-carboxylic acid is obtained as colourless crystal needles of decomposition point 210° C (sealed in vacuo).

In the thin layer chromatogram on silica gel, $Rf_{52A} = 0.15$, $Rf_{101} = 0.36$ and $Rf_{110} = 0.006$. MIC: E.coli = 10 γ/ml; K.pneum. = 6 γ/ml; S.typh. = 10 γ/ml.

In the ultraviolet spectrum (in 0.01 N hydrochloric acid), $\lambda_{max}$ is 263 nm ($\epsilon = 30{,}700$). The optical rotation $[\alpha]_D^{20} = +1°$ (c = 0.98 in 0.05 N hydrochloric acid).

EXAMPLE 7

8.13 Grams of 7-[(para-aminopyridinium)acetylamino]-cephalosporanic acid are dissolved in 350 ml of 5.7% phosphate buffer at pH 6.7by warming to about 30° C. Then 5.28 g of solid 5-mercapto-3-methyl-1,2,4-thiadiazole are added, the pH is adjusted to 6.5 with 10% dipotassium hydrogen phosphate solution an the mixture is warmed gently, in the process of which the entire substance goes into solution. The solution is then stirred under nitrogen for 6 hours at 60° C and upon cooling to 0° C, is passed into 4 litres of methanol of 0° C while stirring vigorously. Stirring is continued for half an hour at 0° C and crystallised phosphate is filtered off. The filtrate is initially concentrated in vacuo to a volume of about 800 ml and water removed therefrom by concentrating it in vacuo to a volume of 400 ml while adding continuously a total of 3 litres of absolute ethanol (through capillaries). Finally, 800 ml of ethyl acetate are added thereto and the resulting mixture is left to stand for 1 hour at 0° C and filtered. The filter residue is washed with ethyl acetate; this crude precipitate (9.86g) still contains phosphate. It is dissolved in 25 ml of water; after addition of 50 ml of chloroform and vigorously shaking crystallisation commences. The crude crystalline product is separated and dissolved in 100 ml of a mixture of 2 parts by volume of methanol and one part by volume of water, the solution stirred with activated carbon (registered trademark "Norit"), filtered through a layer of diatomaceous earth (registered trademark "Hyflo") and the filtrate concentrated in vacuo until the onset of the precipitation of amorphous particles. The concentrate is then warmed to 25° C and vigorously shaken upon addition of 50 ml of chloroform, when crystals immediately precipitate. The batch is concentrated in vacuo to a total volume of about 50 ml and left to stand for 2 hours at 0°. The precipitate is filtered off, the crystal cake washed with absolute ethanol and dried under high vacuum.

The 7-[(para-aminopyridinium)acetylamino]-3-(3-methyl1,2,4-thaidiazol-5-ylthio)methyl-ceph-3-em-4-carboxylic acid is thereby obtained in the form of colourless crystal needles which have a decomposition point of 172° C (fused in vacuo). The crystals contain 0.5 mol of chloroform very firmly combined.

In a thin-layer chromatogram on silica gel: $Rf_{52A} = 0.14$, $Rf_{69}$ (ethyl acetate/acetic acid/water 60:20:20) = 0.21, $Rf_{101} = 0.41$ and $Rf_{110} = 0.10$. MIC: St.aureus 511 = 0.1 γ/ml; St. aureus 2999 = 0.1 γ/ml; B.meg. = 10 γ/ml.

In an ultra-violet spectrum (in methanol/water 2:1) $\gamma_{max}$ 273 nm ($\epsilon = 34{'}500$). The optical ratation $[\alpha]_D^{20} = +26° \pm 1°$ (c = 1.14 in methanol/water 2:1).

EXAMPLE 8

0.9 Gram of 7-bromoacetylamino-3-(1-methyl-tetrazol-5-yl-thio)methylceph-3-em-4-carboxylic acid is dissolved in 5 ml of methanol with the addition of 0.35 ml of N,N-diisopropylethylamine. 0.42 Gram of 4-tert.-amyloxycarbonylaminopyridine dissolved in 1.4 ml of methanol is added and the solution is left to stand for 14 hours at room temperature. The reaction mixture is then filtered and evaporated in vacuo to a foam. This foam residue is dissolved in 10 ml of ethanol and precipitated in the form of a flocculent, colourless precipitate by rapidly adding 150 ml of absolute ether. The batch is left to stand for half an hour at room temperature, filtered with suction, the filter product washed with ether and dried in vacuo. The residue is dissolved in the 10-fold amount of a mixture of 19 parts by volume of chloroform and 1 part by volume of ethanol, the solution filtered and the 7-[(4-tert.amyloxycarbonyl-aminopyridinium)acetylamino]-3-(1-methyl-tetrazol-5-ylthio)methylceph-3-em-4-carboxylic acid is obtained in the form of a colourless precipitate by rapidly adding 50 parts by volume of ether.

In a thin-layer chromatogram on silica gel: $Rf_{52A}$ = 0.26, $Rf_{101}$ = 0.53; $Rf_{69}$ = 0.39 (with iodine spray).

To remove the protective group, this product is dissolved in the 5-fold amount of trifluoroacetic acid, the solution left to stand for a brief time and then the product is precipitated by squirting the solution into ether. It is washed repeatedly with ether to yield the trifluoroacetate in the form of an almost colourless precipitate. This precipitate is dissolved in water, the pH adjusted to 5 by addition of dilute aqueous ammonia solution, and the solution is concentrated to a small volume and the product precipitated with ethanol. The precipitate is separated and dissolved in a small mixture of water and methanol (1:1), filtered and precipitated once more with excess ethanol, to give the 7-[(4-aminopyridinium)acetylamino]-3-(1-methyl-tetrazol-5-ylthio)methylceph-3-em-4-carboxylic acid which is identical with the substance described in Example 1.

The starting material can be manufactured as follows:

50 Grams of 4-aminopyridine are dissolved in a sulphonating flask (2.5 litre capacity) in a mixture of 160 ml of dioxan and 160 ml of water and the solution is cooled to 0° C. Then, while stirring vigorously and with further cooling, 480 ml of a toluene solution which contains 95 g of tert. amyloxycarbonyl chloride are passed in within about 5 minutes. The reaction takes place within 24 hours after slowly warming the whole solution to room temperature and continuously adding 2N sodium hydroxide solution (total of 390 ml) while keeping the pH at 10.

The two phases are separated, the toluene phase is washed repeatedly with concentrated sodium chloride solution, dried with sodium sulphate, and evaporated in vacuo to give the reaction product in crude crystalline form. The aqueous phase is re-extracted with chloroform and yields a small amount of additional material.

The combined extracts are dissolved in 100 ml of ethanol, filtered, concentrated in vacuo to a volume of about 25ml and the concentrate is treated slowly with 60 ml of water while stirring and seeding, in the process of which the 4-tert.amyloxycarbonyl-aminopyridine crystallises in colourless needles. Melting point: 107°–108° C.

In a thin-layer chromatogram on silica gel: $Rf_{52A}$ = 0.48; $Rf_{110}$ = 0.86; $Rf_{101}$ = 0.69 (with iodine spray). In the ultra-violet spectrum (in ethanol) $\lambda_{max}$ = 242 nm($\epsilon$ = 19'800).

EXAMPLE 9

50.8 Grams of 7-[(para-aminopyridinium)acetylamino]-cephalosporanic acid and 29.0 g of 5-mercapto-1-methyl-tetrazole are suspended in 300 ml of water and, by addition of 800 ml of 10% dipotassium hydrogen phosphate solution, dissolved and the pH adjusted to 6.5. The solution is then stirred under nitrogen for 6 hours at 60° C. After it has cooled to 0° C, the solution is passed into 11 litres of methanol of −5° C while stirring vigorously and the pH is adjusted ot 7.7 by addition of 50 ml of 20% phosphoric acid. Stirring is continued for half an hour at 0° C and crystallised phosphate is filtered off. The filtrate is concentrated initially in vacuo to a volume of about 2 litres and water removed therefrom by concentrating in vacuo to a volume of about 1.6 litres while continuously adding a total of 3 litres of absolute ethanol (through capillaries). The solution is decanted off from the pale brown resin which has precipitated on the side of the flask. The decantate is mixed with 1.8 litres of ethanol while stirring and then with 3.6 litres of ethyl acetate. The batch is left to stand for 1 hour at 0° C, filtered, the filtrate washed with ethyl acetate to give a precipitate which is almost pure. This precipitate is dissolved in 40 ml of water, the pH adjusted to 6.2 with 1.1 ml of N hydrochloric acid and the solution is vigorously shaken for about ½ hour after adding 55 ml of chloroform and 20 ml of ethanol, when crystallisation soon commences. The crystalline product is separated, dissolved in the 15-fold volume of a mixture of one part by volume of ethanol and 9 parts by volume of water, the solution filtered and the filtrate brought to a volume of about 40–50 ml by carefully concentrating it in vacuo or by lyophilisation. The concentrate is vigorously shaken after adding 50 ml of chloroform and 20 ml of ethanol, when crystals immediately form. The batch is left to stand for 2 hours at 0° C and the crystals are filtered off. The crystal cake is washed with a small amount of 80% ethanol and then with absolute ethanol and dried in vacuo.

The 7-[(para-aminopyridinium)acetylamino]-3-(1-methyl-tetrazol-5-ylthio)methylceph-3-em-4-carboxylic acid is obtained in the form of colourless crystal needles having a decomposition point of 171° C (fused in vacuo).

The values which are obtained in thin-layer chromatogram on silica gel, ultra-violet spectrum and optical rotation, coincide with those given in Examples 1 and 2.

EXAMPLE 10

1.01 Grams of 4-tert. amyloxycarbonyl-aminopyridiniumacetic acid are dissolved in 6 ml of dimethyl formamide, the solution is diluted with 6 ml of tetrahydrofuran, treated with 0.453 ml of triethylamine, cooled to −10° C and treated dropwise with 0.42 ml of chloroformic acid isobutyl ester. A solution (cooled to 0° C) of 1.23 g of 7-amino-3-(1-methyl-tetrazol-5-ylthio)methylceph-3-em-4-carboxylic acid and 0.488 ml of triethylamine in a mixture of 5 ml of tetrahydrofuran and 5 ml of water is added after 15 minutes. The reaction mixture is further stirred for 1 hour at 0° C and 1½ hours at room temperature, the pH is adjusted to 6.5 and the tetrahydrofuran distilled off in vacuo. The residual solution is pre-extracted with 80 ml of ethyl acetate and the extract discarded, then extracted with 3 × 100 ml of a mixture of ethyl acetate and ethanol (4:1). The organic phase is dried with sodium sulphate and evaporated to dryness in vacuo. The residue is extracted with chloroform, the extract decolourised with a small quantity of activated carbon ("Norit"), and filtered through a short column of Hyflo Supercel. The filtrate is concentrated to a small volume and, by addition of ether in excess, the 7-[(4-tert. amyloxycarbonyl-aminopyridinium)acetylamino]-3-(1-methyltetrazol-5-ylthio)methylceph-3-em-4-carboxylic acid is obtained in the form of a slightly coloured precipitate which, in a thinlayer chromatogram on silica gel, responds in the same manner as the substance described in Example 8: $Rf_{52.1} = 0.26$; $Rf_{69} = 0.39$; $Rf_{101} = 0.53$ (with iodine spray).

The protective group is removed by means of the process used in Example 8.

The 4-tert.amyloxycarbonyl-aminopyridiniumacetic acid can be manufactured as follows:

A solution of 2.47 g of 4-tert.amyloxycarbonylaminopyridine in 3.5 ml of absolute methanol is added to a solution of 2.18 g of bromethyl acetate in 2 ml of absolute methanol and the batch is left to stand overnight at room temperature.

The solvent is evaporated and a semi-solid, pale yellow residue is obtained. This residue is dissolved in 20 ml of absolute ethanol and cooled in an acetone/dry ice bath. The reaction product is crystallised in colourless needles by slowly adding a total of 200 ml of absolute ether while stirring vigorously. The crystalline product is filtered with suction, washed with ethanol/ether (1:9) and absolute ether and dried immediately in a vacuum exsiccator. The pure bromide of the 4-tert.amyloxycarbonyl-aminopyridinium ethyl acetate melts in the evacuated capillary with decomposition at 94° C and turns brown at 210° C.

In a thin-layer chromatogram on silica gel; $Rf_{52} = 0.49$; $Rf_{110} = 0.52$; $Rf_{101} = 0.6$ ( staining with iodine spray).

3.39 Grams of 4.tert.amyloxycarbonyl-aminopyridinium ethyl acetate are dissolved in 15 ml of ethanol and 5 ml of water and sufficient 2N sodium hydroxide solution is added dropwise to attain a pH of 10. The solution is left to stand overnight and then adjusted to pH 6 with 2N hydrochloric acid. It is subsequently concentrated to a small volume and the sodium chloride which has formed is precipitated by addition of ethanol. This operation is repeated, when the 4-tert-.amyloxycarbonylaminopyridiniumacetic acid is obtained finally on evaporating the filtrate in vacuo.

Thin-layer chromatogram on silica gel: $Rf_{52} = 0.39$; $Rf_{110} = 0.33$; $Rf_{101} = 0.51$ (iodine spray).

The 7-amino-3-(1-methyl-tetrazol-5-yl-thio)methyl-ceph-3-em-4-carboxylic acid can be manufactured as follows:

490 mg of anhydrous sodium salt of 7-(D-5-aminoadipoulamide)-3-(1-methyl-1H-tetrazol-5-ylthio)methylceph-3-em-4-carboxylic acid (manufactured according to Dutch Patent No. 6 806 179) are suspended in 30 ml of absolute methylene chloride and the suspension is treated with 0.4 ml of absolute pyridine and 0.92 ml of trimethylchlorosilane. The suspension is stirred vigorously under nitrogen for 2 hours at 30° C. Upon addition of 1.0 ml of pyridine, the reaction solution is cooled to −15° C and treated in small amounts with 6.55 ml of a 10% solution of phosphorus pentachloride in methylene chloride (internal temperature not above −10° C). The milky solution is stirred for a further 40 minutes at about −12° C. The reaction solution is again cooled to −15° C and 12.0 ml of absolute methanol is passed in small amounts, in the process of which the internal temperature rises to −10° C. The batch is left for 30 minutes at this temperature and allowed to react for a further 30 minutes at +25° C.

The hydrolysis is performed by adding 1.5 ml of 50% aqueous formic acid and the pH adjusted by adding a small amount of triethylamine (app. 0.9 ml) to 2.0. The batch is stirred for 45 minutes at room temperature, when a fine precipitate forms. The pH is brought 4.0 by adding more triethylamine and the reaction mixture is left to stand for about 2 hours in an ice bath. The precipitate is filtered with suction, washed with a small quantity of water, then with methanol and finally with ether, to yield the 7-amino-3-(1-methyl-1H-tetrazol-5-ylthio)methylceph-3-em-4-carboxylic acid (m.p.175° C with decomp.).

What we claim is:

1. Compounds of the general formula I

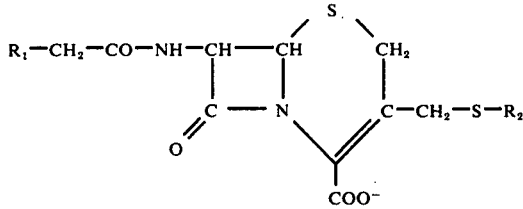

wherein $R_1$ denotes an aminopyridinium radical of the formula

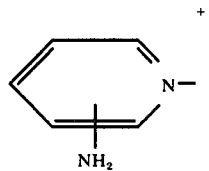

and $R_2$ represents a heterocyclic radical of aromatic character having 5 to 6 ring atoms which is bonded via a carbon atom to the sulphur atom and contains at least 2 nitrogen atoms and a sulphur atom said heterocyclic radical being unsubstituted or substituted by lower alkyl, lower alkoxy, lower alkylthio, cyclopentyl, cyclohexyl, unsubstituted phenyl, substituted phenyl, unsubstituted thienyl, substituted thienyl, the substituents of phenyl and thienyl being nitro, halogen, lower alkyl or lower alkoxy, and therapeutically acceptable salts of these compounds.

2. Compounds of the formula I as claimed in claim 1, wherein $R_1$ represents the para-aminopyridinium radical and $R_2$ represents a thiadiazole radical which is unsubstituted or substituted by lower alkyl, lower alkoxy, lower alkylthio, cyclopentyl, cyclohexyl, unsubstituted phenyl, substituted phenyl, unsubstituted thienyl, substituted thienyl, the substituents of phenyl and thienyl being nitro, halogen, lower alkyl or lower alkoxy.

3. A compound as claimed in claim 1, wherein $R_1$ is para-aminopyridinium and $R_2$ is 3-methyl-1,2,4-thiadiazol-5-yl, and therapeutically acceptable salts thereof.

4. A compound as claimed in claim 1, wherein $R_1$ is para-aminopyridinium and $R_2$ is a member selected from the group consisting of 1,3,4-thiadiazol-5-yl and 2-methyl-1,3,4-thiadiazol-5-yl, and therapeutically acceptable salts thereof.

5. Compounds of the formula I as claimed in claim 1, wherein $R_1$ denotes an aminopyridinium radical of the formula

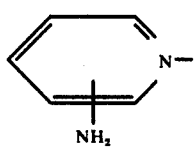

and $R_2$ represents a heterocyclic radical of aromatic character having 5 ring atoms which is bonded to the sulphur atom via a carbon atom and contains 2 nitrogen atoms and a sulphur atom, said heterocyclic radical being unsubstituted or substituted by lower alkyl, lower alkoxy, lower alkylthio, cyclopentyl, cyclohexyl, unsubstituted phenyl, substituted phenyl, unsubstituted thienyl, substituted thienyl, the substituents of phenyl and thienyl being nitro, halogen, lower alkyl or lower alkoxy, and therapeutically acceptable salts of these compounds.

* * * * *